United States Patent [19]

Büyüktimkin et al.

[11] Patent Number: 6,118,020
[45] Date of Patent: Sep. 12, 2000

[54] CRYSTALLINE SALTS OF DODECYL 2-(N,N-DIMETHYLAMINO)-PROPIONATE

[75] Inventors: Servet Büyüktimkin; Nadir Büyüktimkin, both of Lawrence, Kans.

[73] Assignee: NexMed Holdings, Inc., Robbinsville, N.J.

[21] Appl. No.: 09/314,571

[22] Filed: May 19, 1999

[51] Int. Cl.$^7$ ................................................. C07C 229/12
[52] U.S. Cl. .......................................................... 560/155
[58] Field of Search ............................................. 560/155

[56] References Cited

U.S. PATENT DOCUMENTS

| 4,980,378 | 12/1990 | Wong et al. | 514/785 |
| 5,082,866 | 1/1992 | Wong et al. | 514/785 |

OTHER PUBLICATIONS

Chemical Means of Transdermal Drug Permeation Enhancement in *Transdermal and Topical Drug Delivery Systems*, Ghosh T. K., Pfister W.R., Yum S.I. (Eds.), Interpharm Press Inc., Buffalo Grove, IL (1997).

"Alkyl N,N–Disubstituted–Amino Acetates", Büyüktimkin, N., et al., pp. 91–102, in *Percutaneous Penetration Enhancers*, CRC Press, Inc., 1995.

Article, "Synthesis and Enhancing Effect of Dodecyl 2–(N,N–Dimethylamino)propionate on the Transepidermal Delivery of Indomethacin, Clonidine, and Hydrocortisone", Büyüktimkin, N., et al., pp. 1632–1637, appearing in "Pharmaceutical Research," vol. 10, No. 11, 1993.

Abstract No. 2686, *1997 AAPS Annual Meeting Contributed Papers Abstracts*, American Association Of Pharmaceutical Scientists.

Kirk–Othmer Encyclopedia of Chemical Technology, 4th ed., vol. 9, John Wiley & Sons, NY, 1994, pp. 774–776.

*Primary Examiner*—Samuel Barts
*Assistant Examiner*—Brian J. Davis
*Attorney, Agent, or Firm*—Olson & Hierl, Ltd.

[57] ABSTRACT

Dodecyl 2-(N,N dimethylamino)-propionate (DDAIP) is prepared by transesterification of ethyl 2-(N,N-dimethylamino) propionate. Crystalline acid addition salts of DDAIP are prepared by cooled mixing of DDAIP with one of a select group of acids in the presence of a water immiscible solvent such as hexane. The resulting DDAIP salts are crystalline, and exhibit a pattern of defined detection peaks upon analysis by powder x-ray diffraction.

18 Claims, 2 Drawing Sheets

6,118,020

CRYSTALLINE SALTS OF DODECYL 2-(N,N-DIMETHYLAMINO)-PROPIONATE

TECHNICAL FIELD

This invention relates to crystalline acid addition salts of dodecyl 2-(N,N-dimethylamino)-propionate (DDAIP), their preparation and their use as skin penetration enhancers.

BACKGROUND OF THE INVENTION

The advantages of transdermal drug delivery over other methods of drug administration are well recognized. Working alone, most drugs do not sufficiently permeate the skin to provide therapeutic levels of drug delivery. The skin, especially the outer layer (stratum corneum), provides a formidable barrier to the penetration of most substances. To overcome the skin's natural protective barrier, topical drug formulations typically include a skin penetration enhancer. Skin penetration enhancers also may be referred to as absorption enhancers, accelerants, adjuvants, solubilizers, sorption promoters, etc. Whatever the name, such agents serve to improve drug absorption across the skin. Ideal penetration enhancers not only increase drug flux across the skin, but do so without irritating, sensitizing, or damaging skin. Furthermore, ideal penetration enhancers should not adversely affect the stability of the active drug, the physical stability of the dosage form (e.g. cream or gel), or the cosmetic quality of the topical composition.

A wide variety of compounds have been evaluated as to their effectiveness in enhancing the rate of penetration of drugs through the skin. See, for example, Büyüktimkin et al., Chemical Means of Transdermal Drug Permeation Enhancement in *Transdermal and Topical Drug Delivery Systems,* Ghosh T. K., Pfister W. R., Yum S. I. (Eds.), Interpharm Press Inc., Buffalo Grove, Ill. (1997), which surveys the use and testing of various skin penetration enhancers.

Of the many groups of compounds being evaluated, several alkyl (N,N-disubstituted amino alkanoate) esters have shown promise as penetration enhancers. Of the alkyl (N,N-disubstituted amino alkanoate) esters, dodecyl 2-(N,N dimethylamino)-propionate (DDAIP) has shown particular promise because of its confirmed biodegradability. For a discussion of the penetration enhancing properties of DDAIP see Büyüktimkin et al., Alkyl N,N-Disubstituted-Amino Acetates in *Percutaneous Penetration Enhancers,* Maibach H. I. and Smith H. E. (eds.), CRC Press, Inc., Boca Raton, Fla. (1995).

DDAIP, which may also be referred to as dodecyl 2-methyl-2-(N,N-dimethyl amino) acetate, is an effective skin penetration enhancer for a wide variety of medicaments and has the following chemical formula:

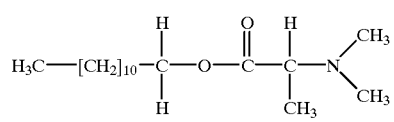

DDAIP is a liquid at room temperature and as such is not easy to purify. DDAIP is not soluble in water, but is miscible with most organic solvents. Table I, below, contains a list of other reported attributes of DDAIP.

TABLE I

Physical Properties Of DDAIP

| | |
|---|---|
| Molecular Weight | 285.47 |
| CAS Number | 149196-89-4 |
| Physical form | Clear colorless liquid |
| Freezing point | −17.5° C. |
| Boiling point | 142–144° C./0.1 mmHG |
| Viscosity | 7.32 centiStokes at 23° C. |
| Refractive Index (nD) | 1.4435 at 24.5° C. |
| Specific gravity ($D_{23}$) | 0.85 |

What is needed is a form of DDAIP that can be readily purified and adapted for use in the variety of dosage forms used for transdermal delivery. Furthermore, what is needed is a reliable cost effective method of manufacturing DDAIP.

SUMMARY OF THE INVENTION

The present invention provides crystalline, acid addition salts of dodecyl 2-(N,N-dimethylamino)-propionate (DDAIP). The addition salts of DDAIP according to the present invention include inorganic acid addition salts such as the hydrochloric, hydrobromic, sulfuric, phosphoric, and nitric acid addition salts, as well as organic acid addition salts such as the acetic, benzoic, salicylic, glycolic, succinic, nicotinic, tartaric, maleic, malic, pamoic, methanesulfonic, cyclohexanesulfamic, picric, and lactic acid addition salts.

Preferred crystalline DDAIP salts are DDAIP hydrogen chloride and DDAIP dihydrogen sulfate.

DDAIP can be conveniently manufactured by transesterification of ethyl 2-(N,N-dimethylamino) propionate. To this end, ethyl 2-(N,N-dimethylamino) propionate is heated with 1-dodecanol in the presence of a transesterification catalyst.

A wide variety of transesterification catalysts are available for this purpose. Preferred are basic transesterification catalysts such as the alkali metal alkoxides, e.g. sodium methoxide, potassium methoxide, and the like. Other suitable basic transesterification catalysts are n-butyl lithium, potassium cyanide, and the like.

The method for the manufacture of such DDAIP acid addition salts comprises combining DDAIP with a selected acid in the presence of a water-immiscible solvent to form a salt precipitate and then recovering the salt precipitate, from solution. The DDAIP is combined with the selected acid at a controlled temperature in the range of about 10° to about −10° Celsius. The water-immiscible solvent is preferably an aliphatic hydrocarbon, more preferably hexane.

DESCRIPTION OF THE EMBODIMENTS

Figure 1:
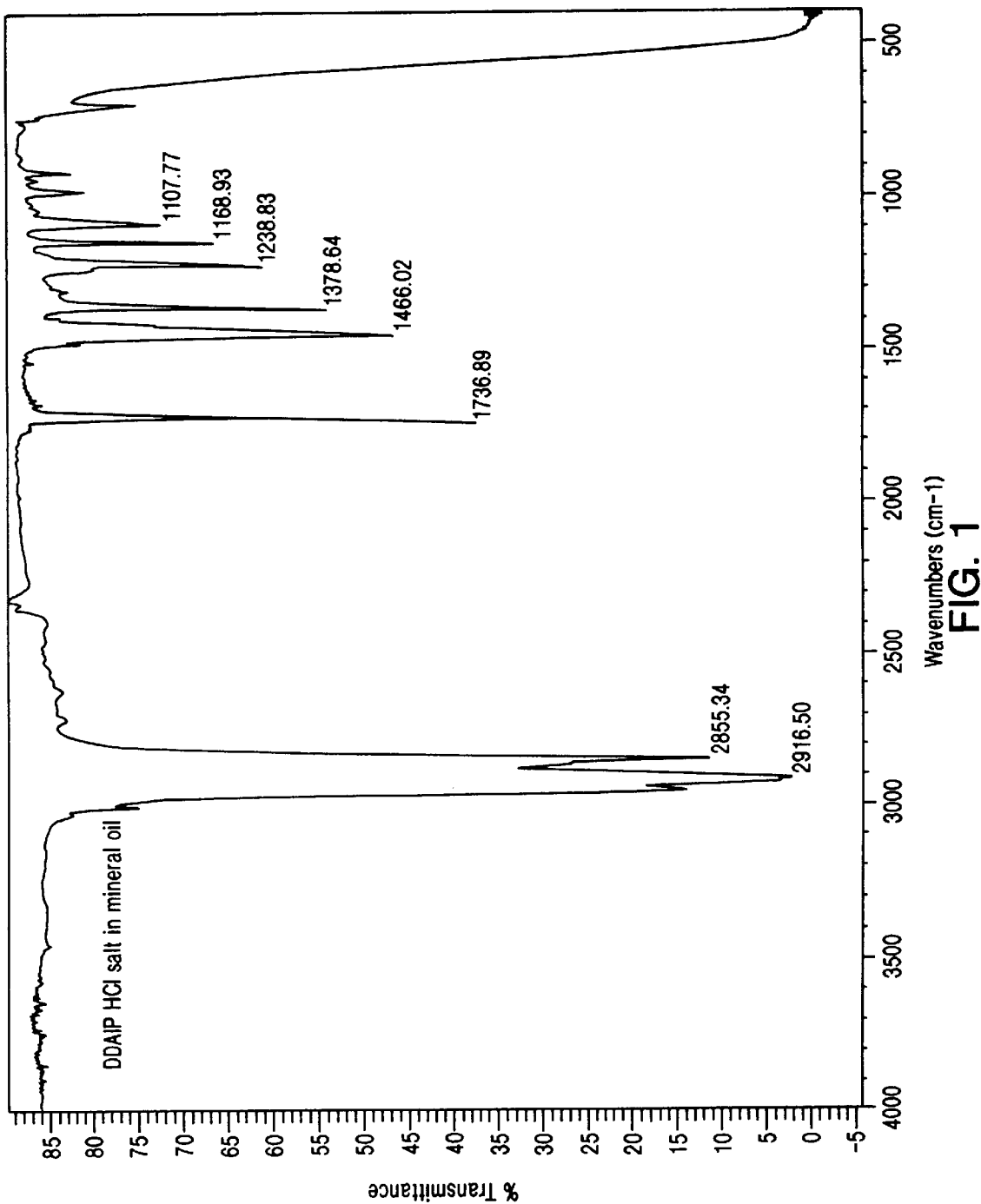
FIG. 1 is an infrared spectrum of a sample of a crystalline hydrochloric acid addition salt of DDAIP (DDAIP.HCl) dispersed in mineral oil.

While this invention is susceptible to embodiments in many different forms, preferred embodiments of the invention are described below. It should be understood, however, that the present disclosure is to be considered as a exemplification of the principles of the invention and is not intended to limit the invention to the specific embodiments illustrated.

Crystalline, acid addition salts of dodecyl 2-(N,N-dimethylamino)-propionate (DDAIP) can be inorganic as well as organic. Representative inorganic acid addition salts include the hydrochloric, hydrobromic, sulfuric, phosphoric, nitric acid addition salts of DDAIP, and their solvates. Exemplary organic acid addition salts include acetic, benzoic, salicylic, glycolic, succinic, nicotinic, tartaric, maleic, malic, pamoic, methanesulfonic, cyclohexanesulfamic, picric, and lactic acid addition salts, as well as their respective solvates.

Preferred among the inorganic acid addition salts are DDAIP hydrogen chloride,

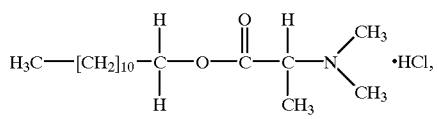

and DDAIP dihydrogen sulfate,

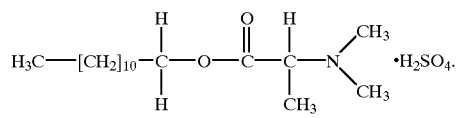

In addition, alkyl-2-(N,N-disubstituted amino)-alkanoates such as DDAIP can be synthesized from readily available starting materials as described in U.S. Pat. No. 4,980,378 to Wong et al., which is incorporated herein by reference to the extent that it is not inconsistent. As described therein, alkyl-2-(N,N-disubstituted amino)-alkanoates are readily prepared via a two-step synthesis. In the first step, long chain alkyl halogenoacetates are prepared by reaction of the corresponding long chain alkanols with halogenomethyl halogenoformates or the like in the presence of an appropriate base such as triethylamine, typically in a suitable solvent such as chloroform. For DDAIP, this reaction can be depicted as follows:

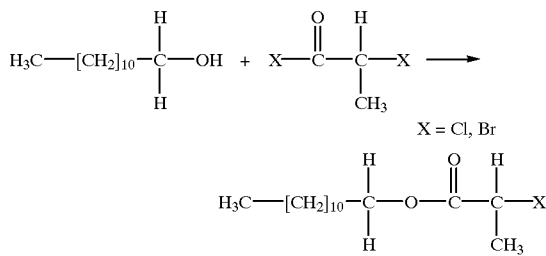

The reaction temperature may be selected from about 10° Celsius to about 200° Celsius or reflux, with room temperature being preferred. The use of a solvent is optional. If a solvent is used, a wide variety of organic solvents may be selected. Choice of a base is likewise not critical. Preferred bases include tertiary amines such as triethylamine, pyridine and the like. Reaction time generally ex tends from about one hour to three days.

In the second step, the alkyl substituted halogenoacetate is condensed with an appropriate amine according to the scheme:

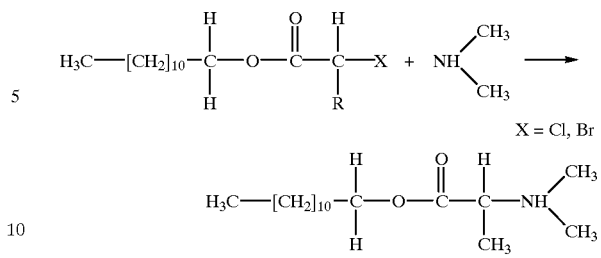

Excess amine reactant is typically used as the base and the reaction is conveniently conducted in a suitable solvent such as ether. This second step is preferably run at room temperature, although temperature may vary. Reaction time usually varies from about one hour to several days.

An alternate and preferred approach to synthesizing DDAIP is the transesterification of ethyl 2-(N,N-dimethylamino)-propionate. Ethyl 2-(N,N-dimethylamino)-propionate can be prepared by reacting commercially available ethyl 2-bromopropionate with dimethylamine followed by distillation to separate unreacted halogenated compounds.

To trigger the transesterification, the ethyl 2-(N,N-dimethylamino)-propionate is heated in the presence of 1-dodecanol and a basic transesterification catalyst such as sodium methoxide. Other suitable basic transesterification catalysts are n-butyl lithium, potassium cyanide, and the like.

Also suitable as transesterification catalysts are acids such as sulfuric acid, p-toluene sulfuric acid, and the like. Still other transesterification catalysts that can be used are boron tribromide, trimethylsilyl iodide, trimethylsilyl iodine, aluminum oxide, tetraisopropyl titanate, molecular sieves containing tert-butanol and potassium tertiary butoxide, Grignard reagents, porcine pancreatic lipase, pig liver esterase, horse liver esterase (with solid support), α-chymotrypsin, silver trifluoroacetate, mercury(II) trifluoroacetate, palladium(II) chloride, mercury(II) acetate with sulfuric acid, mercury(II) chloride (cadmium carbonate), thallium (II) trifluoro acetate, and compounds of the formula X—Sn (n—Bu)$_2$—O—Sn(n—Bu)$_2$—OH, where X is a halogen.

A representative reaction scheme follows:

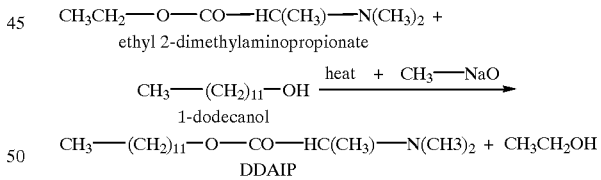

The ethyl 2-(N,N-dimethylamino)-propionate is preferably refluxed for about 2 hours in the presence of 10 percent stoichiometric excess 1-dodecanol and a catalytic amount of sodium methoxide (predissolved in toluene). During this process, the ethanol formed is removed from the reaction medium by azeotropic distillation. Following the reaction phase, the solids of the remaining mixture are filtered off, resulting in a DDAIP filtrate.

The transesterification approach to synthesizing DDAIP results in a product containing relatively lower levels of by-products and unreacted reactants, which are undesirable, often skin-irritating, and difficult to remove by conventional methods.

According to another method aspect of the present invention, DDAIP free base is mixed with a water-immiscible solvent such as hexane to form a reactant solution. The reactant solution is maintained at a temperature in the range of about 10° to about −10° Celsius. Acid is then added to the temperature-controlled solution in an amount sufficient for the formation of a salt precipitate in the reactant solution. During the acid addition, constant stirring (or agitation) of the reactant solution is optional, but preferred. The salt precipitate of DDAIP is recovered by any suitable method such as filtration.

The foregoing method of making DDAIP salts may be utilized as a purification step for removing reaction by-products and unprocessed reactants from DDAIP. Synthesis procedures according to the present invention can result in substantially pure salt precipitates of DDAIP.

The present invention is illustrated by the following examples.

EXAMPLE 1

Preparation Of Hydrochloric Acid Addition Salt Of DDAIP

DDAIP was prepared by transesterification of ethyl 2-(N,N-dimethylamino)-propionate obtained from Varsal Instruments Inc. (Warminster, Pa). Specifically, a mixture ethyl 2-(N,N-dimethylamino)-propionate, 1-dodecanol, and sodium methoxide predissolved in toluene was refluxed for about 2 hours. As ethanol formed, it was removed by azeotropic distillation. After about 2 hours of refluxing, the remaining reaction product was filtered to remove solids.

DDAIP.HCl was prepared by diluting 50 grams of the DDAIP filtrate with 200 milliliters of hexane in a flask, where the hexane and DDAIP were thoroughly mixed. The resulting hexane-DDAIP mixture was cooled to about 50° Celsius. Next, under constant stirring, hydrogen chloride gas was bubbled through the mixture for approximately 2 to 5 minutes, after which a precipitate was noted. The resulting precipitate was recovered by filtration. About 49 grams of precipitate were recovered.

Samples of the recovered substance were analyzed for carbon-nitrogen-hydrogen content, melting point, X-ray powder diffraction spectra, mass spectra, infrared spectra, and nuclear magnetic resonance (NMR) in the $^1$H and the $^{13}$C modes. Before property testing, the recovered precipitate was dissolved in boiling ethyl acetate and then recrystallized by allowing the mixture to cool to room temperature.

An elemental carbon-nitrogen-hydrogen analysis detected 63.29 percent carbon, 4.26 percent nitrogen, and 11.34 percent hydrogen, which generally matched the calculated values of 63.4 percent carbon, 4.3 percent nitrogen and 11.2 percent hydrogen for DDAIP.HCl ($C_{17}H_{35}NO_2$.HCl). Melting point was tested and verified to be in the range of about 88° to about 90° Celsius.

For x-ray powder diffraction testing, a ground sample of DDAIP.HCl was tested using a Siemens D500 Automated Powder Diffractometer equipped with a graphite monochromator and a Cu ($\lambda$=1.54 Å) x-ray source operated at 50 kV and 40 mA. The two-theta scan range was 4° to 40° with a step scan window of 0.05° per 1.2 seconds. Beam slits were set at No. (1)1°, (2)1°, (3)1°, (4)0.15°, and (5)0.15° widths. Well-defined peaks were detected at the following values of two-theta: 19.5°, 21°, 25°, 29.6°.

Mass spectroscopy of a sample dissolved in dichloromethane produced peaks for the largest molecules detected at unit masses of 284 and 286, which compares well to the molecular weight of a DDAIP molecule, about 285.47.

The results of an infrared spectroscopy analysis of a DDAIP.HCl sample (in mineral oil) are presented in FIG. 1.

Data generated by NMR analysis for $^1$H and $^{13}$C spectra did not reveal shifts that are inconsistent with DDAIP.HCl.

EXAMPLE 2

Preparation Of Sulfuric Acid Addition Salt Of DDAIP

DDAIP.H$_2$SO$_4$ was prepared by mixing 200 milliliters hexane with 50 grams of DDAIP prepared as described in Example 1 in a flask, where the hexane and DDAIP were thoroughly mixed together. The resulting hexane-DDAIP mixture was cooled to about 5° Celsius. Concentrated sulfuric acid was then added dropwise under constant stirring to form a precipitate. After adding about 18 grams of sulfuric acid, the stirring was discontinued and the resulting DDAIP.H$_2$SO$_4$ precipitate was separated by filtration. About 60 grams of precipitate were recovered.

Samples were analyzed by the same methods listed in Example 1. Before property testing, the DDAIP.H$_2$SO$_4$ was dissolved in boiling ethyl acetate and recrystallized.

Elemental analysis indicated 53.41 percent carbon, 3.63 percent nitrogen and 9.61 percent hydrogen. These values generally matched the calculated values of 53.23 percent carbon, 3.65 percent nitrogen, 9.72 percent hydrogen for DDAIP.H$_2$SO$_4$ ($C_{17}H_{37}NO_6S$). Melting point was tested and verified to be in the range of about 58° to about 60° Celsius.

For x-ray powder diffraction, a ground sample of DDAIP.H$_2$SO$_4$ was tested using the diffractometer and equipment settings described in Example 1. Well-defined peaks were detected at the following values of two-theta: 13.3°, 16.6°, 21.8°, 23.3°.

Figure 2:
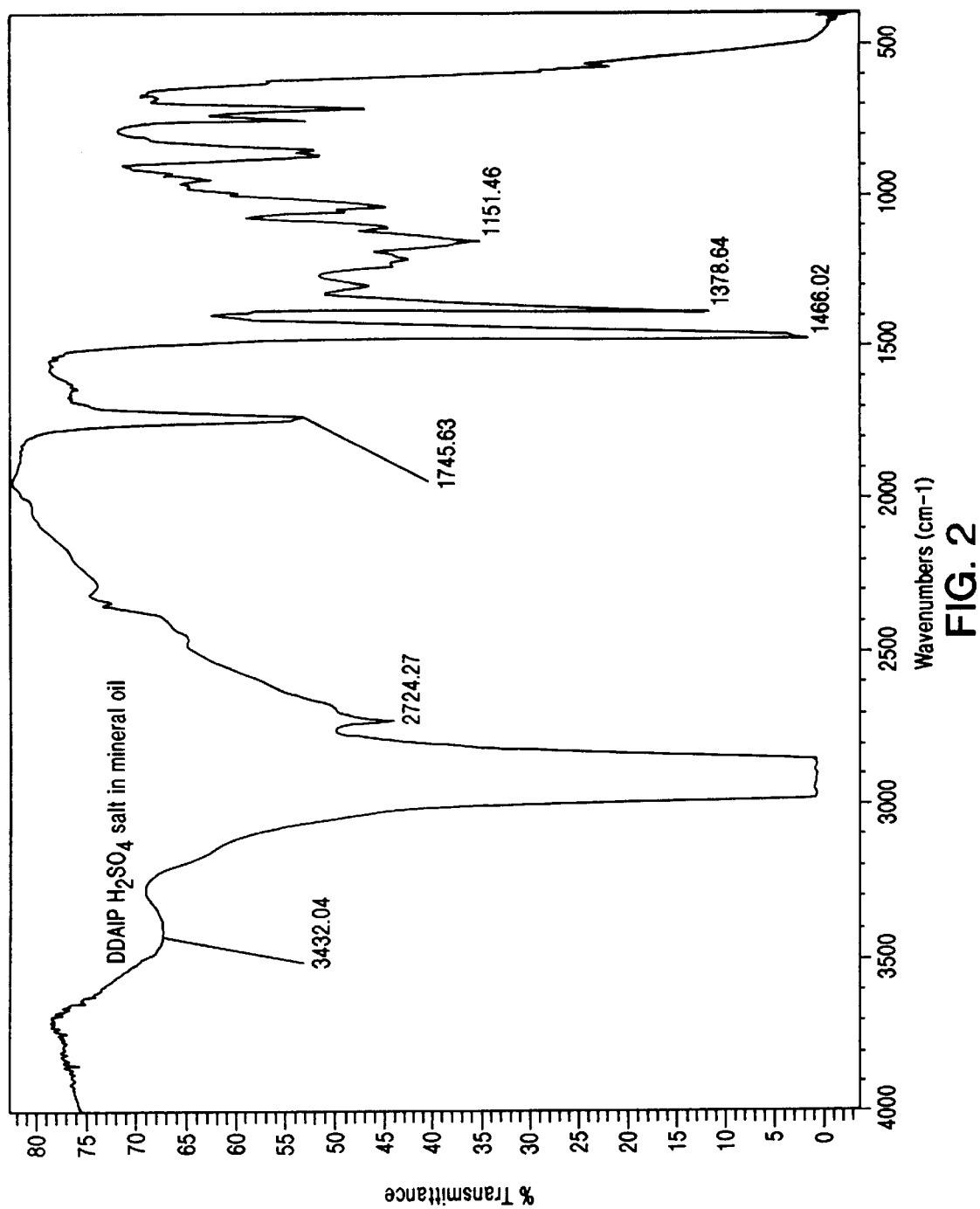
FIG. 2 is an infrared spectrum of a sample of a crystalline sulfuric acid addition salt of DDAIP (DDAIP.H$_2$SO$_4$) dispersed in mineral oil.

Mass spectroscopy of a sample in dichloromethane produced peaks for the largest molecules detected at unit masses of 284 and 286, which compares well to the molecular weight of DDAIP, about 285.47. The results from an infrared spectroscopy analysis are presented in FIG. 2. Data generated by NMR analysis for $^1$H and $^{13}$C spectra did not reveal shifts that are inconsistent with DDAIP.H$_2$SO$_4$.

The foregoing is intended to be illustrative of the present invention, but not limiting. Numerous variations and modifications may be effected without departing from the true spirit and scope of the invention.

We claim:

1. A crystalline salt of dodecyl 2-(N,N-dimethylamino)-propionate.

2. A crystalline inorganic salt of dodecyl 2-(N,N-dimethylamino)-propionate.

3. The crystalline inorganic salt of claim 2 that is selected from the group consisting of the hydrochloric, hydrobromic, sulfuric, phosphoric, and nitric acid addition salts.

4. A crystalline organic salt of dodecyl 2-(N,N-dimethylamino)-propionate.

5. The crystalline organic salt of claim 4 that is selected from the group consisting of the acetic, benzoic, salicylic, glycolic, succinic, nicotinic, tartaric, maleic, malic, pamoic, methanesulfonic, cyclohexanesulfamic, picric, and lactic acid addition salts.

6. Crystalline dodecyl 2-(N,N-dimethylamino)-propionate hydrochloride.

7. The crystalline salt of claim 6 characterized by defined x-ray detection peaks upon analysis by powder x-ray diffraction with a Cu x-ray source at the following values of two-theta: 19.5°, 21°, 25°, 29.6°.

8. Crystalline dodecyl 2-(N,N-dimethylamino)-propionate hydrogen sulfate.

9. The crystalline salt of claim 8 characterized by defined detection peaks upon analysis by powder x-ray diffraction with a Cu x-ray source at the following values of two-theta: 13.3°, 16.6°, 21.8°, 23.3°.

10. A method for the manufacture of crystalline salts of dodecyl 2-(N,N-dimethylamino)-propionate comprising:

combining dodecyl 2-(N,N-dimethylamino)-propionate with an acid in the presence of a water-immiscible solvent and at a temperature of about 10 to about −10° Celsius in an amount sufficient to form a salt precipitate; and recovering the salt precipitate.

11. The method of claim 10 wherein said acid is an inorganic acid.

12. The method of claim 11 wherein said inorganic acid is selected from the group consisting of hydrochloric acid, hydrobromic acid, sulfuric acid, phosphoric acid, and nitric acid.

13. The method of claim 10 wherein said acid is an organic acid.

14. The method of claim 13 wherein said organic acid is selected from the group consisting of acetic acid, benzoic acid, salicylic acid, glycolic acid, succinic acid, nicotinic acid, tartaric acid, maleic acid, malic acid, pamoic acid, methanesulfonic acid, cyclohexanesulfamic acid, picric acid, and lactic acid.

15. The method in accordance with claim 10 comprising the steps of combining said dodecyl 2-(N,N-dimethylamino)-propionate with said water-immiscible solvent to form a reactant solution;

maintaining said reactant solution at a temperature in the range of about 10° to about −10°Celsius;

adding said acid to said reactant solution to form a salt precipitate in said reactant solution; and recovering said salt precipitate.

16. The method in accordance with claim 10 wherein said acid is hydrochloric acid which is mixed with said dodecyl 2-(N,N-dimethylamino)-propionate by bubbling hydrogen chloride gas through a mixture of said dodecyl 2-(N,N-dimethylamino)-propionate and said solvent.

17. The method in accordance with claim 10 wherein said acid is sulfuric acid which is mixed with said dodecyl 2-(N,N-dimethylamino)-propionate by incremental addition of concentrated sulfuric acid to a mixture of said dodecyl 2-(N,N-dimethylamino)-propionate and said solvent.

18. The method in accordance with claim 10 wherein said solvent is hexane.

* * * * *